United States Patent [19]

Sawaya et al.

[11] Patent Number: Plant 6,980

[45] Date of Patent: Aug. 8, 1989

[54] DISTINCT VARIETY OF POINSETTIA NAMED RED SAILS

[75] Inventors: Milhem Sawaya, Simcoe; Michael J. Howe, Delhi, both of Canada

[73] Assignee: Fernlea Flowers, Ltd., Delhi, Canada

[21] Appl. No.: 234,429

[22] Filed: Aug. 19, 1988

[51] Int. Cl.[4] ..... A01H 5/00

[52] U.S. Cl. ..... Plt./86

[58] Field of Search ..... Plt./86

*Primary Examiner*—Robert E. Bagwill

*Attorney, Agent, or Firm*—Webb, Burden, Ziesenheim & Webb

[57] ABSTRACT

A Poinsettia plant named Red Sails is particularly characterized by its brilliant crimson bracts against a background of dark green foliage, its strong, fixed stems and its long lasting keeping qualities in the home. It also has excellent resistance to fade and vigorous growth habits including branch and bract production.

1 Drawing Sheet

BACKGROUND OF THE NEW PLANT

The present invention comprises a new and distinct cultivar of *Euphorbia pulcherrima* known by the varietal name Red Sails.

The new cultivar was discovered in December of 1986 among a large population of Poinsettias including the cultivar Marjo Red at Willowdale, Ontario. It is believed that the new cultivar is a sport of the cultivar Marjo Red. The new cultivar was first asexually reproduced by Fernlea Flowers, Ltd. of Delhi, Ontario in December of 1986 and has been repeatedly asexually reproduced by cuttings by Fernlea Flowers, Ltd. at Delhi, Ontario. Continued observations of the vegetative cuttings have confirmed that the distinguishing features of this cultivar come true, remain stable and are retained through successive propagations.

The following traits are determined to be basic characteristics of this new cultivar which in combination distinguish this Poinsettia as new and distinct:

1. Eight week response time.
2. Dark green foliage.
3. Thick strong stems.
4. Bracts are large in length and width.
5. Bracts are vivid red.
6. Plant produces large number of branches and bracts.
7. Plant grows vigorously.
8. Compact free branching when pinched.
9. Contrast of brilliant crimson bracts against the background of dark green foliage is unique.
10. Same dark green foliage and flowering response as Marjo Red.
11. Bracts up to 4.5 inches wide and 8 inches long.
12. Bracts very long lasting.
13. Outstanding disease resistance.

DESCRIPTION OF THE DRAWING

The accompanying photographic drawing illustrates the new cultivar, the color being as nearly true as possible with color descriptions of this type.

DESCRIPTION OF THE NEW PLANT

The following detailed description set forth the characteristics of the new culivar. The data which defines these characteristics were collected from asexual reproductions carried out in Delhi, Ontario. The plant history was taken on eight week plants. The test plants were grown under normal greenhouse conditions and color readings were taken under natural greenhouse light. Color references are from the Exotica International Pictorial Encyclopedia of Exotic Plants Series No. 4.

The plant:

*Form.*—Compact, free branching when pinched.

*Growth habit.*—Thick strong stems; short internodes; needs very little growth regulation.

*Rooting habit.*—Very fast rooting and disease resistant.

*Blooming habit.*—Same as Marjo Red.

*Blooming season.*—Same as Marjo Red, best grown at 62 to 66 degrees Fahrenheit.

Foliage:

*Size.*—Width: 3 to 4 inches. Length: 6 to 8 inches.

*Color.*—New foliage — Upper side, 83 Fern Green. Under side, 76 Meadow Green. Mature Foliage — Upper side, shade darker than 70 Ivy Green. Under side, 77 Forest Green. Leaf Petiole — 35 Garnet Lake.

*Shape.*—Pointed lobes, broad.

*Texture.*—Fleshy. Upper side, smooth, velvety. Under side, smooth evenly veined.

*Edge of margin.*—Slightly serated.

*Ribs and veins.*—Color — 31 Carmine.

*Disease resistance.*—Outstanding.

Flower:

*Quantity.*—12 to 18 cyathia per stem.

*Color.*—3 Canary.

*Size.*—Average to less than average.

*Shape.*—Slightly flat.

Bracts:

*Size.*—Large. Width (in bloom): 4.5 inches. Length (in bloom): 8 inches.

*Shape.*—Wide with short point.

*Texture.*—Upper side, velvety. Under Side, smooth.

*Color.*—Upper side, very bright 32 Crimson. Under side, 31 Carmine.

*Resistance to fade.*—Excellent.

*Quantity.*—12 to 15.

*Veins.*—Small, hardly noticeable on upper side.

Reproductive organs:

*Stamens.*—Quantity — Numerous. Color — 28 Cardinal Red. Size — Small.

*Pollen cups.*—Color — 2 Mimosa.
*Styles.*—Color — 28 Cardinal Red.
*Ovaries.*—Color — Near 73 Grass Green.
*Nectar cups.*—Color — 2 Mimosa.

I claim:

1. A new and distinct variety of Poinsettia plant as herein shown and described, and particularly characterized by its brilliant crimson bracts against a background of dark green foliage, its strong, fixed stems, its long lasting keeping qualities in the home, its excellent resistance to fade, vigorous growth habits and its branch and bract production.

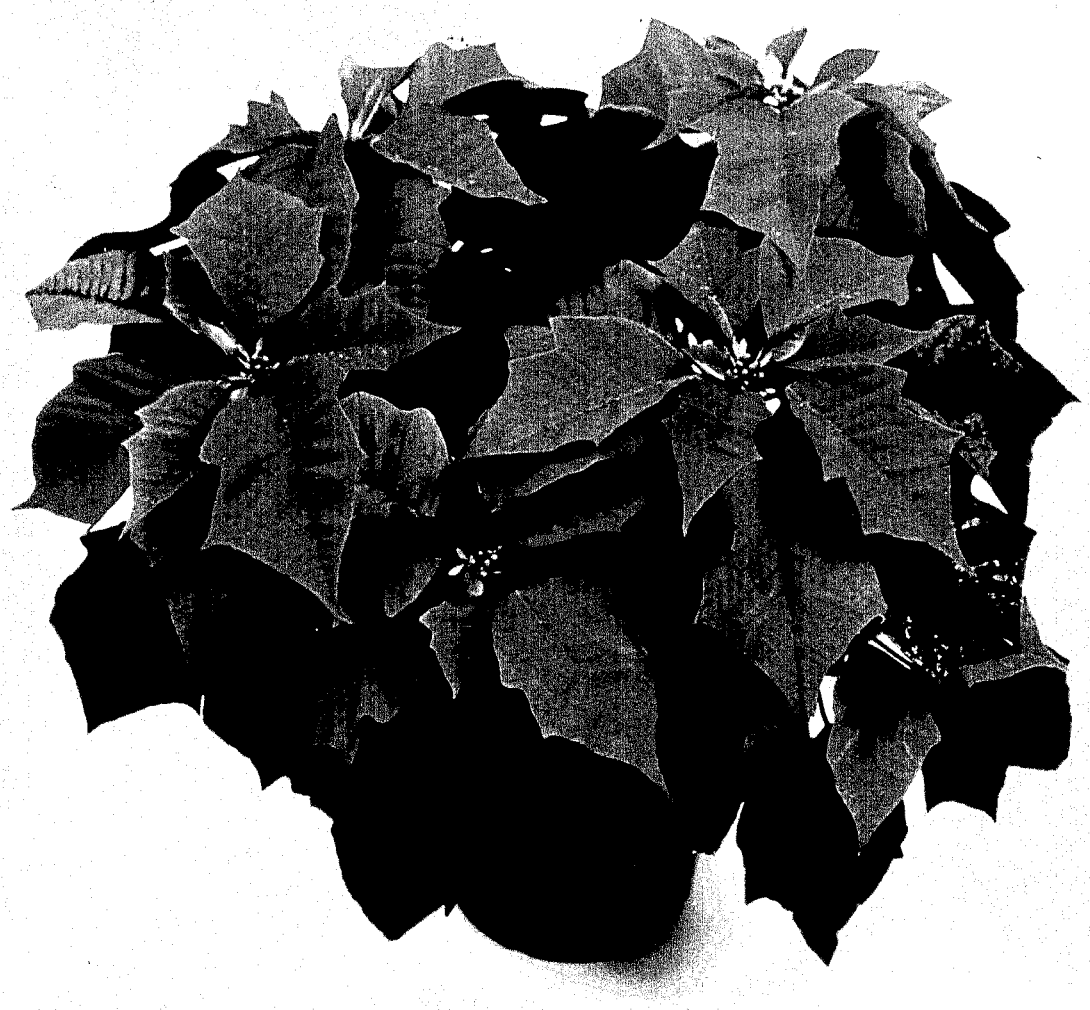

* * * * *